(12) United States Patent
Iffland

(10) Patent No.: US 7,411,665 B2
(45) Date of Patent: Aug. 12, 2008

(54) METHOD FOR WAVELENGTH CALIBRATION OF AN OPTICAL MEASUREMENT SYSTEM

(75) Inventor: Thomas Iffland, Jena (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 190 days.

(21) Appl. No.: 11/329,434

(22) Filed: Jan. 11, 2006

(65) Prior Publication Data

US 2006/0158649 A1 Jul. 20, 2006

(30) Foreign Application Priority Data

Jan. 18, 2005 (DE) .................. 10 2005 002 267

(51) Int. Cl.
*G01N 21/00* (2006.01)
*G01C 25/00* (2006.01)
(52) U.S. Cl. .............. 356/73; 356/243.1; 356/369; 356/448; 356/630; 702/104
(58) Field of Classification Search ............ 356/73, 356/243.1, 243.4, 243.8, 319, 320, 322, 369, 356/448, 630; 702/85–107
See application file for complete search history.

(56) References Cited

U.S. PATENT DOCUMENTS

| 5,771,094 | A | 6/1998 | Carter et al. |
| 6,381,009 | B1 * | 4/2002 | McGahan ............... 356/73 |
| 6,504,608 | B2 * | 1/2003 | Hallmeyer et al. ....... 356/369 |
| 6,567,213 | B2 | 5/2003 | Rosencwaig et al. |
| 7,253,887 | B2 * | 8/2007 | Wolf et al. ............. 356/73 |
| 2004/0239933 | A1 * | 12/2004 | Opsal et al. ............ 356/369 |

* cited by examiner

*Primary Examiner*—Tarifur Chowdhury
*Assistant Examiner*—Tara S Pajoohi
(74) *Attorney, Agent, or Firm*—Simpson & Simpson, PLLC

(57) ABSTRACT

An optical measurement system having a spectrophotometer and a ellipsometer is calibrated, the spectrophotometer and the ellipsometer first being calibrated independently of one another. A spectrophotometer layer thickness ($d_{photo}$) of a specimen is then determined at an initial angle of incidence ($\theta_{init}$) using the spectrophotometer. An ellipsometer layer thickness ($d_{elli}$) of the specimen is then determined using the layer thickness determined with the ellipsometer. The spectrophotometer and the ellipsometer are matched to one another by varying the initial angle of incidence ($\theta_{init}$) until the absolute value of the difference between the spectrophotometer layer thickness ($d_{photo}$) and the ellipsometer layer thickness ($d_{elli}$) is less than a predefined absolute value.

8 Claims, 2 Drawing Sheets

METHOD FOR WAVELENGTH CALIBRATION OF AN OPTICAL MEASUREMENT SYSTEM

CROSS REFERENCE TO RELATED APPLICATIONS

This application claims priority of the German patent application 10 2005 002 267.7, filed on Jan. 18, 2005 which is incorporated by reference herein.

FIELD OF THE INVENTION

The invention relates to a method for wavelength calibration of an optical measurement system having a spectrophotometer and an ellipsometer.

BACKGROUND OF THE INVENTION

In semiconductor fabrication, a plurality of layers are applied to or removed from wafers during the fabrication process. The layers can also be provided in special test regions within a plurality of identical recurring pattern elements. With increasing integration density, requirements in terms of the quality of the layers applied onto the wafers also rise. This means that during the production of a wafer with its plurality of process steps and plurality of layers to be applied (e.g. $SiO_2$, $SiNO_3$, polysilicon, etc., or the like), reliable detection of layer thicknesses must be possible. The existing art discloses a plurality of optical measurement arrangements, operating on the principle of spectrophotometry, for measuring layer thicknesses and associated material parameters. For this, a broadband light beam is focused almost perpendicularly onto the specimen, and the reflected light component is measured. In the spectrograph, that light component is in turn imaged via a grating in wavelength-selective fashion onto a CCD chip. Using a model that contains the optical parameters of the specimen as a function of wavelength, the parameters can be determined by way of a fit to the theoretical spectrum.

These measurement arrangements can be used in particular when thin layers and their optical parameters, for example the refractive index or extinction factor of single- or multilayer systems, need to be measured on wafers. In wafer manufacture specifically, the effort toward ever-thinner layers also means more stringent requirements in terms of the accuracy of the optical measurement arrangement with which the layers can be checked for exactness.

Also known from the existing art for performing such measurements are spectroellipsometers. With these, both the layer thickness and the optical parameters of transparent layers can be determined very accurately. This is done by directing a linearly polarized broadband light beam onto the specimen at an angle. The reflected beam is examined using an analyzer and a spectrograph to identify changes in polarization. The analyzer rotates, allowing only the particular light component that is vibrating in the corresponding polarization plane to strike the spectrograph. That light component is split in wavelength-selective fashion in a spectrograph using a grating, and imaged onto a CCD chip. The spectrum that is obtained then, by way of a model, allows filtration of the optical parameters and the layer thickness.

In order to obtain accurate measurement results, the above-described optical systems usually must first be calibrated. One possibility for calibrating a spectrophotometer is proposed in U.S. Pat. No. 5,771,094, in which a light source having a plurality of spectral lines is used. These spectral lines are imaged onto a CCD, and the lines are each allocated to specific pixels of the CCD. This results in an allocation of the pixel position on the CCD to the known wavelengths of the spectral lines, so that the relationship or calibration function between each pixel on the CCD and the associated wavelength value is determined. The calibration can be further verified by subsequent measurement of a known specimen.

In order to enhance measurement accuracy and, if applicable, to obtain additional information about the specimen, it is known from the existing art to use optical combination devices with which it is possible to carry out two or more examination methods. In this context, in particular, an ellipsometer and a spectrophotometer are advantageously implemented in one device. An optical measurement system for this purpose is known from U.S. Pat. No. 6,567,213. This combination measurement system allows results from the various measurement systems that are present to be combined, thus yielding more accurate results. A prerequisite for good results, however, is that an exact calibration of the measurement systems be performed before the specimens are measured. This is usually done by measuring a known substrate using all the available optical measurement methods, and calibrating each measurement method using the known specimen data.

Because an independent calibration of the two measurement devices leads to differences in measured values, exclusive use of the known calibration methods for such cases leads to unsatisfactory results.

SUMMARY OF THE INVENTION

It is therefore the object of the present invention to propose a method for calibrating an optical measurement system that comprises an ellipsometer and a spectrophotometer, with which the agreement between the data or measured values ascertained with the ellipsometer and with the spectrophotometer can be improved.

According to the present invention, this object is achieved by a method for calibrating an optical measurement system comprising the steps:
calibrating the spectrophotometer and the ellipsometer being independently of one another in an initial calibration,
ascertaining upon calibration of the spectrophotometer, an allocation of the wavelength ($\lambda$) incident onto a CCD chip to the position of the pixels of the CCD chip,
determining a layer thickness ($d_{elli}$) of the specimen using the ellipsometer, as a reference measured value;
determining a spectrophotometer layer thickness ($d^{vis}_{photo}$) in the visual spectral region and a spectrophotometer layer thickness ($d^{UV}_{photo}$) in the UV region, at an initial angle of incidence ($\theta_{init}$);
modifying coefficients of a wavelength-dependent function until the absolute value of the difference between a re-measured visual spectrophotometer layer thickness ($d^{vis}_{photo}$) and a re-measured UV spectrophotometer layer thickness ($d^{UV}_{photo}$) is less than a predefined absolute value; and
varying the initial angle of incidence ($\theta_{init}$) until the absolute value of the difference between the visual spectrophotometer layer thickness ($d^{vis}_{photo}$) and the ellipsometer layer thickness ($d_{elli}$), and the absolute value of the difference between the UV spectrophotometer layer thickness ($d^{UV}_{photo}$) and the ellipsometer layer thickness ($d_{elli}$), are less than a predefined absolute value.

In the context of the method according to the present invention, it is assumed that the spectrophotometer and the ellipsometer are calibrated independently of one another using suitable methods. Then, firstly the layer thickness of a layer is determined using the spectrophotometer of the optical system. Then the thickness of the layer is determined using the ellipsometer, which after being calibrated yields very accurate values for the layer thickness. According to the present invention, the values that are obtained with the spectrophotometer and the ellipsometer are then matched to one another in such a way that the difference between the layer thicknesses measured with the two devices drops below a value acceptable for measurement. For that purpose, the angle of incidence of the spectrophotometer is varied until an angle is found at which the spectrophotometer yields measurement results with which this condition is met. That angle of incidence of the spectrophotometer is maintained for further measurements, and the optical system is calibrated with respect to its components.

In a preferred embodiment of the invention, any optical aberrations of the spectrophotometer that may be present are eliminated by the fact that the measurement results in the visible spectral region (VIS) and in the ultraviolet spectral region (UV) are matched to one another in such a way that the difference between the results drop below a predefined value. Ideally, it is possible thereby to make the values coincident. To achieve this, the wavelength calibration of a spectrophotometer is performed using a light source that covers the spectral region from approximately 190 nm to 800 nm. A gas discharge lamp, for example, is suitable for this. The resulting allocation of the respective wavelengths $\lambda$ to the associated position of the pixels on the CCD chip can be represented as a quadratically fitted function F(Pixpos) of the pixel position. The function F(Pixpos) can then be adapted, by varying the quadratic coefficients, in such a way that sufficient agreement between the measurement results in UV and in VIS can be attained. This is preferably achieved when the deviation of the layer thicknesses $d^{uv}_{photo}$ and $d^{vis}_{photo}$ within a layer thickness interval of the layer thickness that is to be measured is less than a predefined tolerance value.

The advantage of the method according to the present invention is that production-related differences in the angles of incidence of the spectrophotometers, and optical aberrations in the spectrograph, can now be compensated for. A sufficiently accurate matching of the individual optical devices in a combination device can thereby be achieved, those devices then being matched to one another for measurement purposes.

BRIEF DESCRIPTION OF THE DRAWINGS

Further advantages and advantageous embodiments of the invention are the subject matter of the Figures that follow and the descriptions thereof, exact-scale reproduction having been dispensed with in the depictions for the sake of clarity. In the individual Figures.

DETAILED DESCRIPTION OF THE INVENTION

In an embodiment of the invention, firstly the ellipsometer is calibrated in a wavelength region from 320 nm to 800 nm, as is known per se from the existing art. A gas discharge lamp is used as the illumination source for this. The result of the calibration can then be verified on a set of calibration specimens for 25-nm, 285-nm, and 1030-nm $SiO_2$ layers on silicon. The ellipsometer is thereby very accurately calibrated to a layer thickness measurement.

Figure 1:
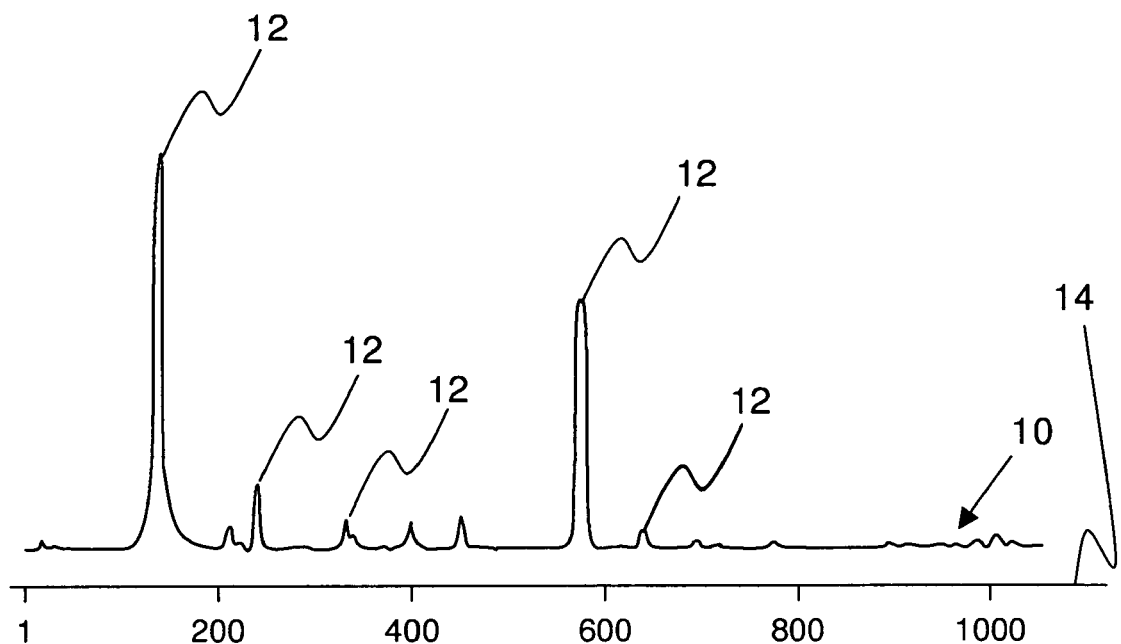
FIG. 1 schematically shows an optical spectrum with allocation to the CCD pixels.

The spectrophotometer is also calibrated, although this wavelength calibration is carried out at wavelengths in the region between 190 nm and 800 nm. A gas discharge lamp is preferably also used for this purpose. The spectrum of the calibration lamp is imaged onto the CCD chip, which can be embodied as a linear or matrix CCD and in each case has pixels. One possible spectrum 10 of an argon calibration lamp is schematically depicted in FIG. 1. This spectrum 10 exhibits peaks 12 whose location, i.e. wavelength, is known on the basis of the lamp that is used. By way of an allocation of these known peaks 12 to the pixels that are plotted on pixel axis 14, calibration can be performed over the entire wavelength region and pixel region.

Figure 2:
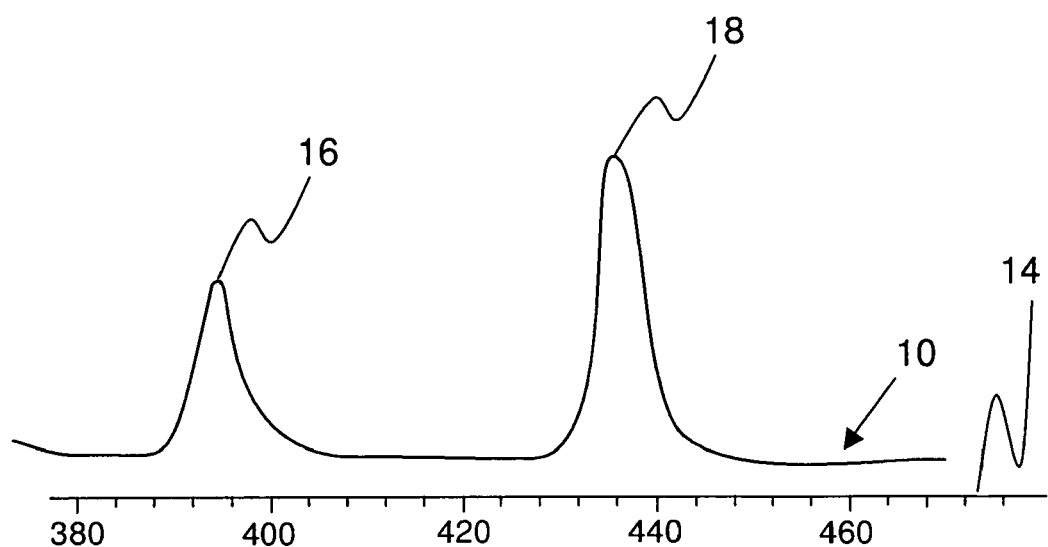
FIG. 2 schematically shows a portion of FIG. 1 in the region between two exemplifying peaks.
Figure 3:
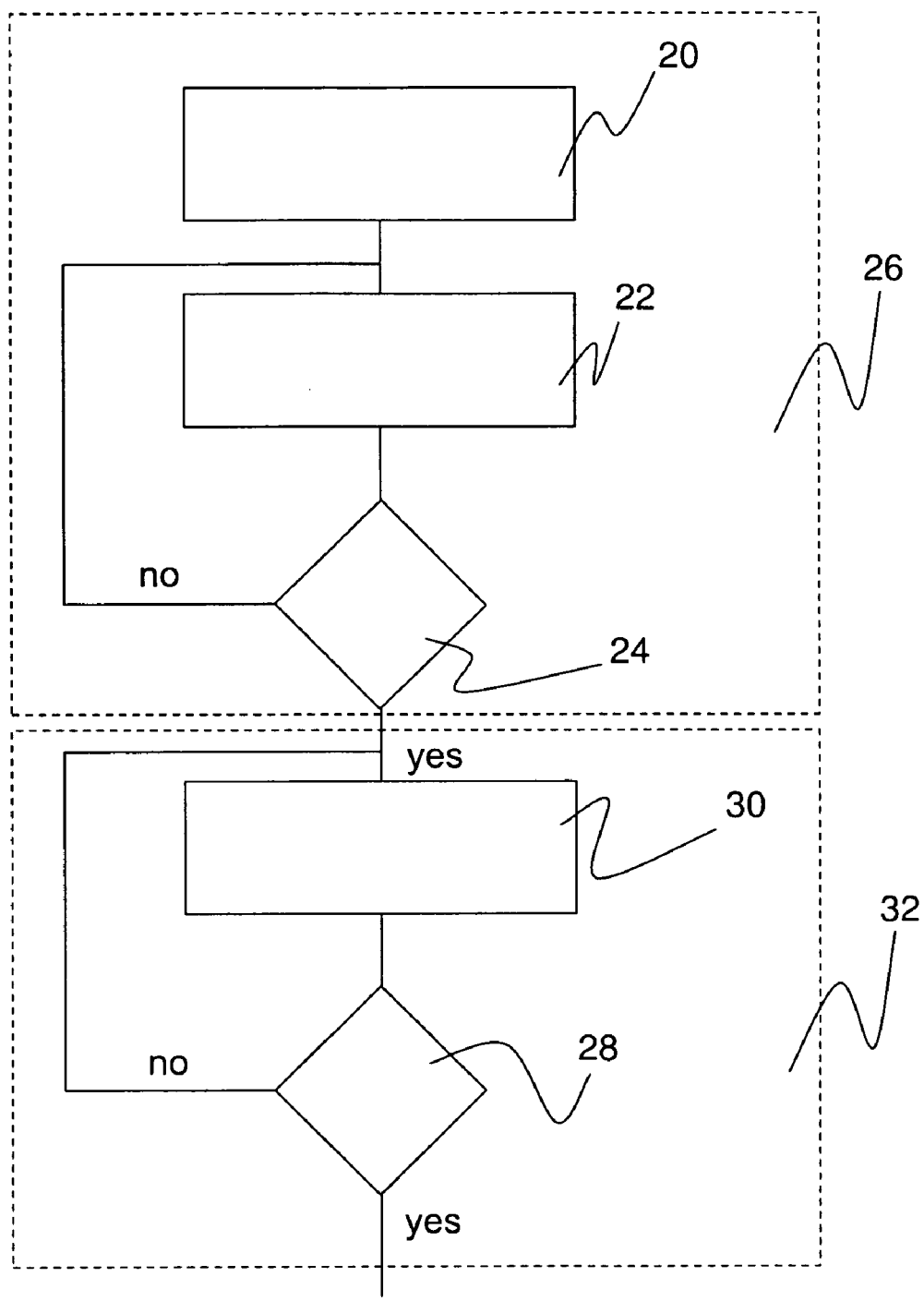
FIG. 3 schematically shows the process sequence for calibrating the optical system.

As depicted in FIG. 2 in an enlarged portion, for this purpose the location of the peaks is ascertained with an accuracy that is better than the spacing of the pixels, i.e. with subpixel accuracy. In the case of first peak 16 and second peak 18 shown by way of example, the pixel position of first peak 16 is identified as 398.394 and that of second peak 18 as 451.787. A so-called peak finder program is used to allow this accuracy to be achieved. FIG. 3 schematically depicts the execution of the method according to the present invention. Following initial calibration 20 as described, the position of peak 12 on CCD yields value pairs (wavelength $\lambda$ and pixel). These value pairs can be represented on the CCD as a function of wavelength in the following form:

$$\lambda(\text{pixel}) = a_0 \cdot (\text{pixel})^2 + b_0 \cdot (\text{pixel}) + c_0.$$

In step 22, coefficients $a_0$, $b_0$, $c_0$ can be fitted, and the resulting measured values can be determined. Coefficients $a_0$, $b_0$, $c_0$ can be obtained, for example using a method of minimum mean error squares. As an example, the table below presents value pairs for twelve wavelength peaks and their corresponding actual positions, as well as their theoretically ascertained reference positions on the CCD chip:

| Item no. | Wavelength (nm) | Reference position (pixels) | Actual position (pixels) |
| --- | --- | --- | --- |
| 1 | 184.91 | 18.9 | 11.148 |
| 2 | 253.65 | 128.2 | 123.943 |
| 3 | 296.73 | 196.7 | 194.327 |
| 4 | 313.16 | 222.8 | 220.717 |
| 5 | 435.84 | 417.9 | 418.92 |
| 6 | 507.30 | 531.5 | 533.221 |
| 7 | 546.08 | 593.2 | 594.606 |
| 8 | 593.46 | 668.5 | 669.619 |
| 9 | 626.32 | 720.7 | 721.068 |
| 10 | 6.965 | 832.4 | 832.457 |
| 11 | 763.51 | 938.9 | 937.819 |
| 12 | 811.53 | 1015.2 | 1021.511 |

The values $a_0 = 1.7045 \cdot 10^{-5}$, $b_0 = 0.60859$, and $c_0 = 178.02129$ were taken as the basis for the coefficients.

Proceeding from the theoretically ascertained correlation between wavelength $\lambda$, the location of pixels 12, and coefficients $a_0$, $b_0$, $c_0$, the accuracy of the spectrophotometer can be further improved by minimizing the difference resulting from measurement of a layer thickness in a sample in UV and in VIS, until that difference drops below a predefined value. This so-called difference calibration 26 of the spectrophotometer is achieved by varying the coefficients $a_0$, $b_0$, $c_0$. A $SiO_2$ layer having a thickness of approximately 1000 nm is particularly suitable for this purpose. When this layer thickness is then measured with the spectrophotometer in UV and in VIS, thickness values $d_{UV\_0}$ and $d_{VIS\_0}$ with coefficients $a_0$, $b_0$, $c_0$ are obtained. From these values, the difference $d_{SP\_0} = d_{VIS\_0} - d_{VIS\_0}$ can be ascertained. To match the spectrophotometer, step 24 checks whether this difference is less than a predefined value, in particular less than 20% of the specification value for the above-described specimen. For the specimen selected, the difference must therefore be less than 5 nm. If this is not the case, in step 22 new values are calculated for coefficients $a_1 = a_0 + \Delta$, $b_1 = b_0 + \Delta$, and $c_1 = c_0 + \Delta$, $\Delta$ having been selected appropriately on the basis of empirical experience. Using the new coefficients, the fit of the measured values obtained can then be recalculated for the function $$\lambda(\text{pixel}) = a_1 \cdot (\text{pixel})^2 + b_1 \cdot (\text{pixel}) + c_1,$$

and once again the difference in layer thicknesses $d_{SP\_1} = d_{VIS\_1} - d_{VIS\_1}$ can be determined. This method is then iteratively repeated until coefficients $a_n$, $b_n$, $c_n$ are obtained for which the difference in layer thickness $d_{SP\_n}$ is less than the requisite value, in particular less than a threshold value that changes as a function of one layer thickness interval. This method then ensures that substantially identical values are obtained with the spectrophotometer in both wavelength regions (UV and VIS).

In the so-called device difference calibration step 32, a thickness value ascertained using the spectrophotometer is then equalized with the thickness value ascertained using the ellipsometer. The formula for determining the layer thickness d on the spectrophotometer incorporates the angle of incidence $\theta$. Without going into more detail as to the meaning of all the variables, this correlation can be stated as $$R^P = \frac{r_{12}^P + r_{23}^P \cdot \exp(-j2\beta)}{1 + r_{12}^P + r_{23}^P \cdot \exp(-j2\beta)} \text{ and } R^S = \frac{r_{12}^S + r_{23}^S \cdot \exp(-j2\beta)}{1 + r_{12}^S + r_{23}^S \cdot \exp(-j2\beta)}$$

$$\text{where } \beta = 2\pi \left(\frac{d}{\lambda}\right) \tilde{N}_2 \cos\Theta_2.$$

In step 30, therefore, an initial angle $\theta_{init}$ is first used for the layer thickness measurement with the spectrophotometer, and the measurement of the layer thickness d of a specimen is performed with the spectrophotometer at that angle and with the ellipsometer. A photometer layer thickness $d_{photo}$ and an ellipsometer layer thickness $d_{elli}$ are ascertained. In step 28, the device difference is calculated by comparing the two variables $d_{photo}$ and $d_{elli}$ to one another. If the difference D (device difference) between the layer thicknesses $D = d_{photo} - d_{elli}$ is less than a predefined value, the calibration is then complete. If the value is greater, a new value for $\theta_n = \theta_{init} + \partial$ is defined, with which value the procedure is repeated. Device comparison 28 is then continued iteratively until device difference D is sufficiently small that substantially identical values are obtained with the spectrophotometer and with the ellipsometer.

When calibration of the combination device is complete, the latter can be used for measurement, and both the spectrophotometer and the ellipsometer will yield substantially identical values for the layer thickness.

What is claimed is:

1. A method for wavelength calibration of an optical measurement system having a spectrophotometer and a ellipsometer, comprising the steps of:
    calibrating the spectrophotometer and the ellipsometer being independently of one another in an initial calibration,
    ascertaining upon calibration of the spectrophotometer, an allocation of the wavelength ($\lambda$) incident onto a CCD chip to the position of the pixels of the CCD chip,
    determining a layer thickness ($d_{elli}$) of a specimen using the ellipsometer, as a reference measured value;
    determining a spectrophotometer layer thickness ($d^{vis}_{photo}$) in the visual spectral region and a spectrophotometer layer thickness ($d^{UV}_{photo}$) in the UV region, at an initial angle of incidence ($\theta_{init}$);
    modifying coefficients of a wavelength-dependent function until the absolute value of the difference between a re-measured visual spectrophotometer layer thickness ($d^{vis}_{photo}$) and a re-measured UV spectrophotometer layer thickness ($d^{UV}_{photo}$) is less than a predefined absolute value; and
    varying the initial angle of incidence ($\theta_{init}$) until the absolute value of the difference between the visual spectrophotometer layer thickness ($d^{vis}_{photo}$) and the ellipsometer layer thickness ($d_{elli}$), and the absolute value of the difference between the UV spectrophotometer layer thickness ($d^{UV}_{photo}$) and the ellipsometer layer thickness ($d_{elli}$), are less than a predefined absolute value.

2. The method according to claim 1, wherein upon calibration of the spectrophotometer, the allocation of the position of the pixels of the CCD chip as a function of the wavelength ($\lambda$) is accomplished by way of a function $\lambda(\text{pixel}) = a_0 \cdot (\text{pixel})^2 + b_0 \cdot (\text{pixel}) + c_0$, and the coefficients $a_0$, $b_0$, $c_0$ are accomplished by fitting to the measured values, in particular using a method of minimum mean error squares.

3. The method according to claim 2, wherein the coefficients $a_0$, $b_0$, $c_0$ are varied until the layer thicknesses ($d^{UV}_{photo}$) and ($d^{vis}_{photo}$) within a layer thickness interval are less than a predefined tolerance value.

4. The method according to claim 3, wherein the predefined tolerance value for layer thicknesses less than 10 nm is equal to approximately 0.5 nm.

5. The method according to claim 3, wherein the predefined tolerance value for layer thicknesses greater than 10 nm and less than 100 nm is equal to approximately 0.6 nm.

6. The method according to claim 3, wherein the predefined tolerance value for layer thicknesses greater than 100 nm and less than 500 nm is equal to approximately 2 nm.

7. The method according to claim 3, wherein the predefined tolerance value for layer thicknesses greater than 500 nm is equal to approximately 5 nm.

8. The method according to claim 3, wherein variation of the coefficients $a_0$, $b_0$, $c_0$ is accomplished using a function of the form $a_1 = a_0 + \Delta$, $b_1 = b_0 + \Delta$, and $c_1 = c_0 + \Delta$, $\Delta$ being ascertained empirically.

* * * * *